United States Patent [19]

Henry et al.

[11] 4,362,583

[45] Dec. 7, 1982

[54] 1,9-DIAZIDO-2,4,6,8-TETRANITRO-2,4,6,8-TETRAZANONANE

[75] Inventors: Ronald A. Henry, China Lake; William P. Norris, Ridgecrest, both of Calif.

[73] Assignee: The United States of America as represented by the Secretary of the Navy, Washington, D.C.

[21] Appl. No.: 256,230

[22] Filed: Apr. 21, 1981

[51] Int. Cl.$^3$ .................... C06B 25/34; C07C 117/00
[52] U.S. Cl. ...................... 149/92; 260/349
[58] Field of Search ........................ 149/92; 260/349

[56] References Cited

U.S. PATENT DOCUMENTS

| | | | |
|---|---|---|---|
| 3,873,579 | 3/1975 | Rosher | 260/349 |
| 3,883,374 | 5/1975 | Rosher | 149/19.8 |
| 3,883,377 | 5/1975 | Wright | 149/88 |
| 4,085,123 | 4/1978 | Flanagan et al. | 260/349 |
| 4,141,910 | 2/1979 | Flanagan et al. | 260/349 |

OTHER PUBLICATIONS

March, J., *Advanced Organic Chemistry*, McGraw Hill, New York, 1968, p. 341.
Boyer, J., et al., *Chem. Rev.*, 54, p. 2 (1954).
Smith, P., *The Chemistry of Open-Chain Organic Nitrogen Compounds*, vol. 2, John Wiley, New York, 1966, p. 485.

*Primary Examiner*—Richard A. Schwartz
*Attorney, Agent, or Firm*—R. F. Beers; W. T. Skeer; B. H. Cottrell

[57] ABSTRACT

A new azido compound 1,9-diazido-2,4,6,8-tetranitro-2,4,6,8-tetrazanonane is disclosed, and a method of preparation is disclosed wherein 1,9-dichloro-2,4,6,8-tetranitro-2,4,6,8-tetrazanonane or 1,9-dinitroxy-2,4,6,8-tetranitro-2,4,6,8-tetrazanonane is reacted with sodium azide and dimethylformamide. This new azido compound is useful as an explosive, propellant, or component thereof to modify properties.

2 Claims, 2 Drawing Figures

4,362,583

1,9-DIAZIDO-2,4,6,8-TETRANITRO-2,4,6,8-TETRAZANONANE

BACKGROUND OF THE INVENTION

1. Field of the Invention

This invention relates to a composition of matter and methods for producing same, and is particularly related to an azido compound used as an explosive, a propellant, or as a burn rate modifier.

2. Description of the Prior Art

Modification of standard explosives and propellants is required when applications require different properties. Various materials have been added to the above to modify the properties thereof. Plasticizers can be added to the energetic materials. Burning-rate modifiers such as, for example, lead salts can be added to the energetic materials. Flash supporters have also been added. Even additional oxidizers have been added such as ammonium perchlorate, potassium nitrate, etc. Fuels can be added also. Thus the composition of the energetic materials can be modified by the addition of materials having the desired properties.

Organic azides have been developed for use as fuel replacement for propellants, and as burn rate modifiers.

SUMMARY OF THE INVENTION

Figure 1:
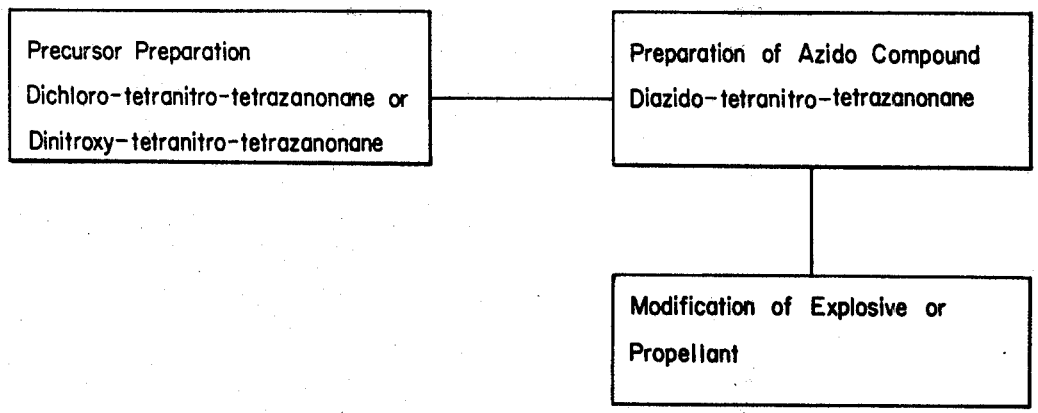
FIG. 1 is a flow diagram with respect to the preparation and use of diazido compound.

A new explosive and propellant is disclosed, 1,9-diazido-2,4,6,8-tetranitro-2,4,6,8-tetrazanonane, having the formula

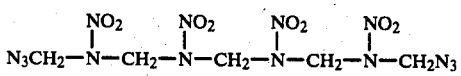

A process to produce this compound is basically composed of mixing 1,9-dichloro-2,4,6,8-tetranitro-2,4,6,8-tetrazanonane or 1,9-dinitroxy-2,4,6,8-tetranitro-2,4,6,8-tetrazanonane with sodium azide and dimethylformamide and heating for a period of time. 1,9-diazido-2,4,6,8-tetranitro-2,4,6,8-tetrazonane is extracted.

It is therefore an object of this invention to provide a new energetic compound having low impact sensitivity.

Another object of this invention is an energetic compound having thermal stability.

Still another object is an energetic compound useful as a burn rate modifier.

An additional object is an energetic composition composed of a standard explosive material and the diazido compound of this invention.

A further object of this invention is to provide a method of preparation of an energetic compound with the aforementioned properties.

Other objects and novel features of the invention will become apparent from the following detailed description.

DESCRIPTION OF THE PREFERRED EMBODIMENT

In order to obtain a precursor compound, 1,9-dichloro-2,4,6,8-tetranitro-2,4,6,8-tetrazanonane, the following procedure was developed. 3 grams of 1,9-diacetoxy-2,4,6,8-tetranitro-2,4,6,8-tetrazanonane was dissolved completely in 200 ml. of dry dioxane with stirring and protection from atmospheric moisture. The solution was cooled to 14°–16° C. until the dioxane began to freeze; then dry, gaseous hydrogen chloride was slowly introduced. As the freezing point dropped, the temperature of the reaction mixture was also gradually lowered to and held at 0°–5° C. When the solution became saturated with hydrogen chloride, the flow of the latter was stopped. The mixture was allowed to stand for 48 hours at 0°–5° C. after which it was resaturated with hydrogen chloride; after another 72 hours, at 0°–5° C. the process was repeated.

Finally after 48 hours, the reaction mixture was concentrated to one-third its original volume at 25 mm. pressure and room temperature. The remaining solution was poured over 100 gm. of ice; the white solid was filtered, washed with cold water until free of acid, and dried. The yield was 2.65 gm(100%), m.p. 196°–197° C.

EXAMPLE I

After the precursor was obtained, 2.65 gm. of it was added to 2.5 gm. of sodium azide and 80 ml. of dimethylformamide. This reaction solution was heated with stirring at 38°–40° C. for 2.5 hours. The solvent was then removed on a rotary evaporator at room temperature and vacuum pump limit; the residue was slurried with 40 ml. of cold water, filtered, washed with cold water and dried. This yielded 2.1 gm. (77%), m.p. 176°–177° C. The m.p. was unchanged after recrystallization from 300 ml. of ethylene dichloride; recovery was 85–90%.

EXAMPLE II

Starting with 1,9-dinitroxy-2,4,6,8-tetranitro-2,4,6,8-tetrazanonane, the same procedure as used in Example I was followed. An 84% yield of material, m.p. 172°–174° C., was obtained. Its infrared spectrum was identical with that for the material from the dichloro precursor.

The calculated analysis for $C_5H_{10}N_{14}O_8$ is C, 15.23; H, 2.56; N, 49.74. Experimentally, the composition was C, 15.40; H, 2.48; N, 49.53.

SUMMARY OF PROPERTIES

Melting Point (Capillary Tube): 176°–177° C. (dec)
Density: 1.67 g./cc.
Impact Sensitivity (50%, 2.5 kg): 19 cm.
DTA (3°/min.): endotherm (m.p.) 167°–168° C.; exotherm starts 173°–174° C.
TGA (3°/min.): Starts to lose weight at 160° C.; by 180°C., it has lost 0.4 mg. out of 21 mg. then at 180° C., all the rest disappears.
$\Delta H_c$ (measured): −2,479 cal./g.
$\Delta H_f$ (calculated): +163.54 kcal./mole.
Detonation Pressure (calculated): 295 kilobars
Detonation velocity (calculated): 8.344 mm./$\mu$ second
Heat of Detonation (calculated): 1506 cal./g.

Figure 2:
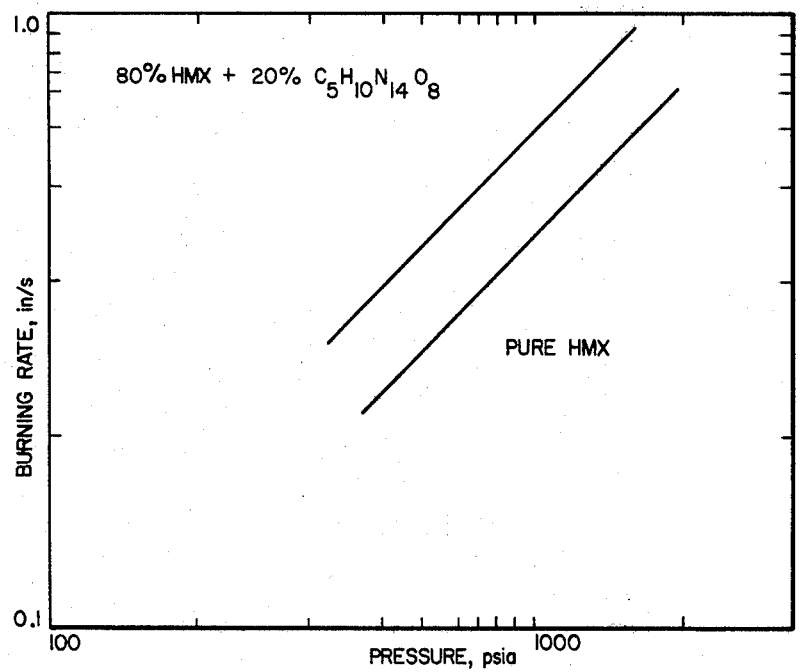
FIG. 2 illustrates the modification of burn rate of HMX with diazido compound.

EXAMPLE III 1,9-diazido-2,4,6,8-tetranitor-2,4,6,8-tetrazanonane was mixed with cyclotetramethylenetetranitramine (HMX) to determine the effect on the burn rate, FIG. 1. 20% by weight of the diazido compound was mixed with HMX. The inclusion of the diazido compound significantly increased the burn rate relative to pure HMX without changing the slope of the burn rate curve of FIG. 2.

Obviously, many modifications of the present invention are possible in light of the above teachings and it is therefore understood that, with the scope of the disclosed inventive concept, the invention may be practiced otherwise than specifically described.

What is claimed is:

1. An azido compound, 1,9-diazido-2,4,6,8-tetranitor-2,4,6,8-tetrazanonane, with the structure $$N_3CH_2-\underset{\underset{NO_2}{|}}{N}-CH_2-\underset{\underset{NO_2}{|}}{N}-CH_2-\underset{\underset{NO_2}{|}}{N}-CH_2-\underset{\underset{NO_2}{|}}{N}-CH_2N_3$$

2. An energetic composition comprising 80% by weight of cyclotetramethylenetetranitramine and 20% by weight of 1,9-diazido-2,4,6,8-tetranitor-2,4,6,8-tetrazanonane.

* * * * *

UNITED STATES PATENT AND TRADEMARK OFFICE
CERTIFICATE OF CORRECTION

PATENT NO. : 4,362,583

DATED : December 7, 1982

INVENTOR(S) : Ronald A. Henry, et al

It is certified that error appears in the above-identified patent and that said Letters Patent is hereby corrected as shown below:

Column 4, line 11, claim 2, "tetranitor" should read -- tetranitro --.

Signed and Sealed this

Twenty-second Day of February 1983

[SEAL]

Attest:

GERALD J. MOSSINGHOFF

Attesting Officer   Commissioner of Patents and Trademarks